US008376976B2

(12) United States Patent
Scott et al.

(10) Patent No.: US 8,376,976 B2
(45) Date of Patent: Feb. 19, 2013

(54) METHOD OF AND APPARATUS FOR WRIST STABILIZATION

(75) Inventors: John Scott, Dallas, TX (US); Leland Duyck, Plano, TX (US)

(73) Assignee: New Options Sports, Dallas, TX (US)

( * ) Notice: Subject to any disclaimer, the term of this patent is extended or adjusted under 35 U.S.C. 154(b) by 164 days.

(21) Appl. No.: 12/104,942

(22) Filed: Apr. 17, 2008

(65) Prior Publication Data
US 2009/0082708 A1    Mar. 26, 2009

Related U.S. Application Data (60) Provisional application No. 60/925,270, filed on Apr. 19, 2007.

(51) Int. Cl.
*A61F 5/00* (2006.01)
*A61F 5/37* (2006.01)
*A41D 13/08* (2006.01)

(52) U.S. Cl. ................. 602/21; 128/846; 2/16
(58) Field of Classification Search ............ 602/16, 602/18, 23, 26–27, 21, 64; 128/846; 2/170, 2/162, 16, 163; 473/54–55; D24/190, 64
See application file for complete search history.

(56) References Cited

U.S. PATENT DOCUMENTS

| 4,854,309 | A | * | 8/1989 | Elsey | 602/21 |
|---|---|---|---|---|---|
| 5,566,389 | A | * | 10/1996 | Li | 2/16 |
| 5,649,800 | A | * | 7/1997 | Hemmersbach et al. | 414/180 |
| 5,649,900 | A | * | 7/1997 | Kline | 602/21 |
| 6,013,045 | A | * | 1/2000 | Gaylord | 602/64 |
| 6,893,410 | B1 | * | 5/2005 | Hely | 602/21 |
| 6,960,176 | B1 | * | 11/2005 | Hely et al. | 602/21 |
| 7,033,331 | B1 | * | 4/2006 | Hely | 602/21 |
| 2002/0193719 | A1 | * | 12/2002 | Yewer, Jr. | 602/21 |
| 2010/0113997 | A1 | * | 5/2010 | Bauerfeind et al. | 602/21 |

* cited by examiner

*Primary Examiner* — Kevin C Sirmons
*Assistant Examiner* — Ophelia A Hawthorne
(74) *Attorney, Agent, or Firm* — Winstead PC (57) ABSTRACT

An orthopedic support device of the type worn on a wrist and a palm of a wearer. The device has a sleeve with an open upper end for receiving the fingers of the wearer, a thumb opening, and an open lower end for receiving the wrist of the wearer. A portion of the sleeve covering the palm of the wearer has a curved configuration. The device also includes, a first strap, designed to be wrapped and secured about a portion of the sleeve covering a palm of the wearer, a second strap designed to be removably wrapped and secured about a portion of the sleeve covering a distal forearm of the wearer, and a third strap, designed to be removably wrapped and secured about a portion of the sleeve covering the wrist of the wearer.

14 Claims, 6 Drawing Sheets

METHOD OF AND APPARATUS FOR WRIST STABILIZATION

CROSS REFERENCE TO RELATED APPLICATIONS

This application claims priority to, and incorporates by reference the disclosure of U.S. Provisional Patent Application No. 60/925,270, filed Apr. 19, 2007, entitled METHOD OF AND APPARATUS FOR WRIST STABILIZATION.

BACKGROUND OF THE INVENTION

1. Field of Invention

The present invention relates to methods of and apparatus for orthopedic support and, more particularly, but not by way of limitation, to an orthopedic support method and apparatus for securing a wrist including an extension portion for a palm region allowing select adjustment for desired restriction of associated hand/wrist movement.

2. History of Related Art

It is common in the Sports Medicine Industry to utilize orthopedic supports for various body parts subject to injury. The most common support areas include, but are not limited to, the knees, elbows, ankles, and wrists. Often injuries to these areas of the body can be treated by the utilization of an appropriate orthopedic support. In the event of surgery, rehabilitation is sometimes augmented by the utilization of such supports.

In addressing the problem of a patient, the best immobilization of the wrist is obtained by wrist supports. By stabilizing the dorsal and palmar aspects of the wrist, flexion, extension, and rotation of the radius and ulnar is prevented. This type of stabilization is typically achieved with traditional splints with palmar and dorsal stays. The carpal and metacarpal bones of the wrist are held stable and radial/ulnar deviations are limited. The best and complete immobilization of the wrist can be obtained via a wrist splint. This type of product is beneficial in post-surgical treatment of wrist injuries.

The products known in the art are typically not easy to adjust and slip onto a user's hand. In addition, the products known in the art are typically made from materials which do not allow air flow. As a result, when a patient wears wrist/thumb splints for extended periods of time, the patient may experience numbness and swelling.

For the aforementioned reasons, there is a need in the art for a method of and apparatus for orthopedic support of a wrist including an extension portion for the palm that overcomes these limitations and provides a new level of flexibility and comfort.

BRIEF SUMMARY OF THE INVENTION

The present invention relates to orthopedic supports and methods. More particularly, one embodiment of the present invention includes an orthopedic support device of the type worn on a wrist and a palm of a wearer. The device comprises a sleeve with an open upper end for receiving the fingers of the wearer, a thumb opening, and an open lower end for receiving the wrist of the wearer. The device also includes, a first strap, designed to be wrapped and secured about a portion of the sleeve covering a palm of the wearer, a second strap designed to be removably wrapped and secured about a portion of the sleeve covering a distal forearm of the wearer, and a third strap, designed to be removably wrapped and secured about a portion of the sleeve covering the wrist of the wearer.

In another embodiment, the present invention comprises an orthopedic support device of the type worn on a wrist, palm, and forearm of a wearer. The device includes a sleeve with an open upper end for receiving the fingers of the wearer, a thumb opening, and an open lower end for receiving the forearm of the wearer. A portion of the sleeve covering the palm of the wearer has a curved configuration. The device also includes, a first strap, designed to be wrapped and secured about a portion of the sleeve covering a palm of the wearer, a second strap designed to be removably wrapped and secured about a portion of the sleeve covering a forearm of the wearer, and a third strap, designed to be removably wrapped and secured about a portion of the sleeve covering the wrist of the wearer.

In another embodiment, the present invention is a method for providing orthopedic stabilization to a wrist of a wearer. First, an orthopedic stabilization device comprising a sleeve and a plurality of straps is provided. Next, the orthopedic stabilization device is placed over the wearer's hand and wrist. Third, stays are inserted into stay pockets at desired locations. Fourth, a first strap is wrapped about the palm of the wearer to a desired compression and secured to the sleeve. Fifth, a second strap is wrapped about the forearm of the wear to a desired compression and secured to the sleeve. Finally, a third strap is wrapped about the wrist of the wearer and secured to the sleeve.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF THE INVENTION

Various embodiments of the present invention will now be described more fully with reference to the accompanying drawings. The invention may, however, be embodied in many different forms and should not be constructed as limited to the embodiments set forth herein; rather, the embodiments are provided so that this disclosure will be thorough and complete, and will fully convey the scope of the invention to those skilled in the art.

Figure 1:
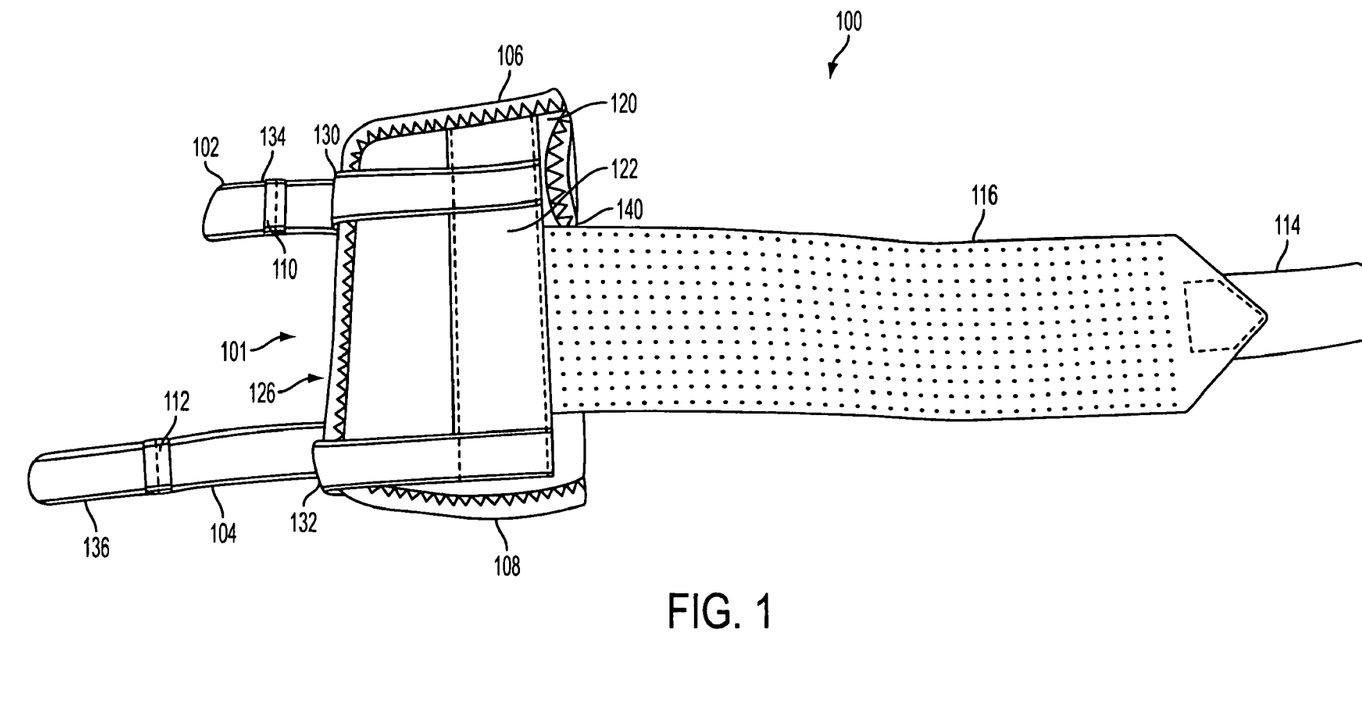
FIG. 1 is a front view of the wrist stabilizer in accordance with a preferred embodiment of the present invention.
Figure 3:
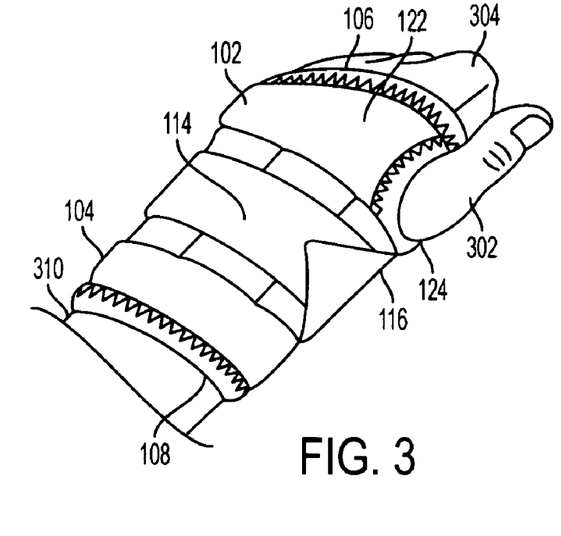
FIG. 3 is a perspective view of the wrist stabilizer placed on a user's hand in accordance with an embodiment of the present invention.

Referring first now to FIG. 1, there is shown a preferred embodiment of a wrist stabilizer 100 of the present invention. For purposes of this disclosure, the term "wrist" shall include both the wrist joint itself, as well as the lowermost portion of the forearm immediately contiguous with the wrist joint, as illustrated in FIG. 3. The wrist stabilizer 100 comprises an upper fastener assembly having a strap 102, a lower fastener assembly having a strap 104, and a central strap 116 having a fastener 114. While only three straps are shown in FIG. 1, it will be understood to one of ordinary skill in the art that any number of straps may be used without departing from the spirit and scope of the present invention. The wrist stabilizer 100 is constructed using any natural or synthetic breathable material, including both inelastic and elastic material, having sufficient flexibility and resiliency. The wrist stabilizer 100 may be formed of, for example, Koolflex™ material which provides durability, elasticity, and air-flow. In another embodiment, the wrist stabilizer 100 may be formed of, for example, two-sided nylon Neoprene. The Koolflex™ material allows the wrist stabilizer 100 to be easily slipped onto a user's hand, and more particularly, the palm and wrist regions. In one embodiment, the Koolflex™ material has a thickness of approximately ⅛ inch.

The upper and lower fastener assemblies comprise loops 130 and 132. The loops 130 and 132 are adapted to allow the straps 102 and 104 to pass through during fastening. The straps 102 and 104 comprise enlarged regions 110 and 112. The enlarged regions 110 and 112 prevent the straps 102 and 104 from becoming undone while using the wrist stabilizer 100. The body of straps 102, 104, and 116 with the exception of fasteners 114, 134, and 136 may be constructed with hook and pile portions to facilitate adjustability and ease of use by the user.

Figure 2:
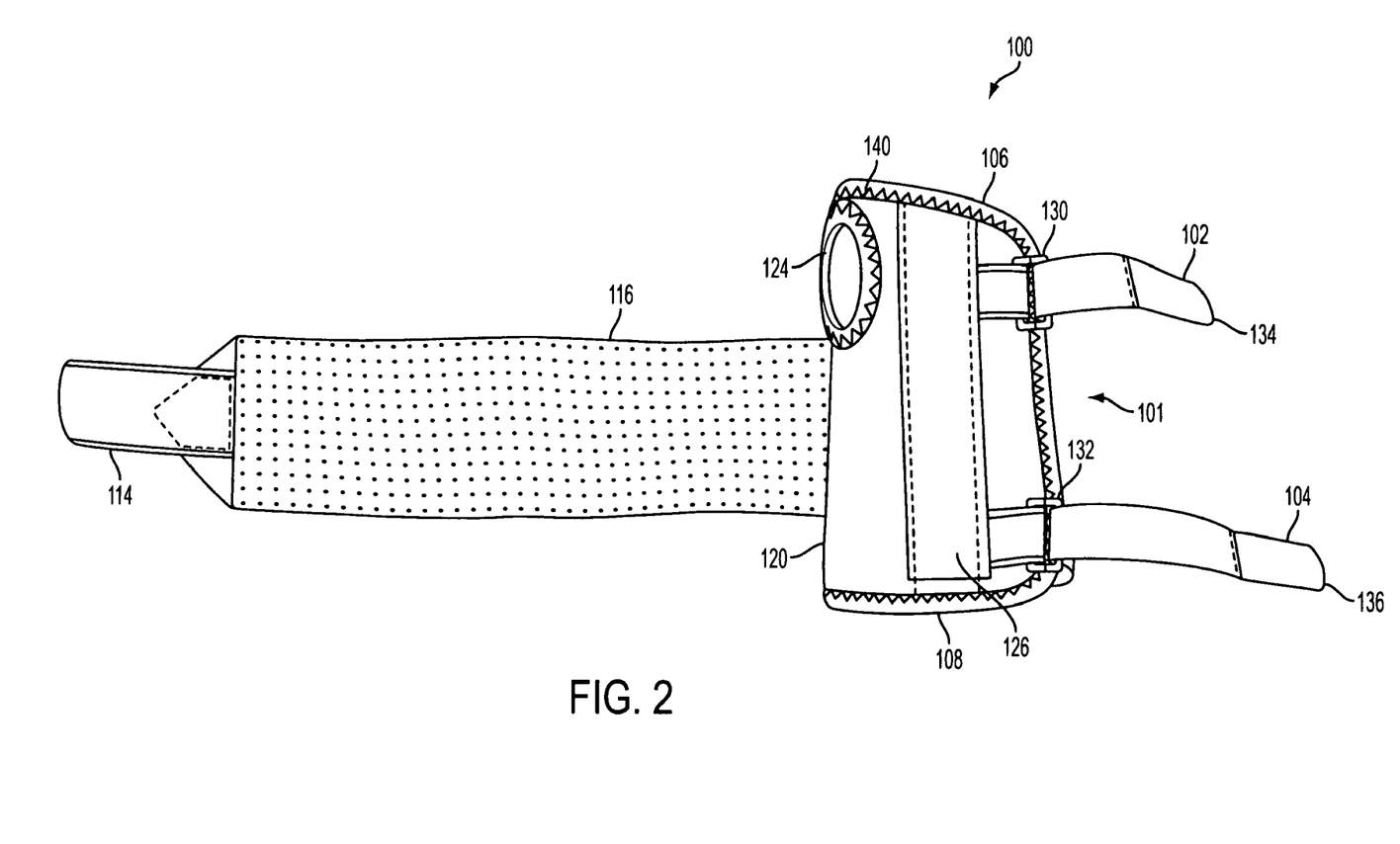
FIG. 2 is a back view of the wrist stabilizer in accordance with a preferred embodiment of the present invention.

Still referring to FIG. 1, the wrist stabilizer 100 includes a sleeve 101 which comprises an open upper-end 106, an open lower-end 108, and a thumb opening 124 (shown in FIG. 2). As described below, the body of straps 102, 104, and 116 with the exception of fasteners 114, 134, and 136 may be constructed with hook and pile portions to facilitate adjustability and ease of use by the user. Once the wrist stabilizer 100 is properly placed over the user's hand, the straps 102 and 104 are wrapped around palm and forearm regions of the user while the strap 116 is wrapped around a wrist region of the user. The length of the straps 102, 104, and 116 are preferably sufficient to encompass the palm, forearm, and wrist regions at least once. It will be appreciated that compression may be adjusted to a desired level by increasing or decreasing the tightness of the straps 102, 104, and 116 around the palm, forearm, and wrist regions.

The central strap 116 having fastener 114 is constructed with hook and pile portions to facilitate adjustability. Once the wrist stabilizer 100 is located on the user's hand, the central strap 116 having the fastener 114 is wrapped around the wrist region of the user. The length of the central strap 116 and the fastener 114 is preferably sufficient to encompass the wrist region at least once. It will be appreciated that compression may be adjusted to a desired level by increasing or decreasing the tightness of the central strap 116 around the wrist region of the user.

Still referring to FIG. 1, the wrist stabilizer 100 further comprises a mesh material 120 adapted to allow the wrist stabilizer 100 to be easily placed on a user's hand. The wrist stabilizer further includes a first stay pocket 122 placed along a medial portion of the wrist stabilizer 100. The first stay pocket 122 is adapted to receive a stay therein for support. The stay may be either a solid stay or a split stay; however, other types of stays may also be used. A second stay pocket 126 is disposed opposite the first stay pocket 122 for receiving a dorsal stay therein for support. The first and second stay pockets 122 and 126 are sewn on the wrist stabilizer 100 and comprise an opening through which the stay may be inserted or removed as desired. Removal of the stay allows for increased mobility and flexibility of the hand and facilitates in the cleaning of the wrist stabilizer 100. Stitching 140 is shown on the edges of the wrist stabilizer 100 as well as stitching 140 shown around the thumb opening 124. This stitching is shown for purposes of illustration only, and other stitching embodiments may be incorporated herein. All illustrations thereof should not be deemed limited in any respect relative to the principles of the present invention.

FIG. 2 is a back view of the wrist stabilizer 100 of FIG. 1 in accordance with an embodiment of the present invention. Details of the wrist stabilizer 100 have been disclosed with respect to FIG. 1 above.

FIG. 3 is a perspective view of the wrist stabilizer 100 placed on a user's hand. The wrist stabilizer 100 is adapted to be slipped onto the user's hand such that the fingers 304 pass through the open upper-end 106 while the thumb 302 passes through the thumb opening 124. The upper strap 102 is adapted to secure a palm region of the users hand while the lower strap 104 is adapted to secure a forearm region 310 of the users hand. The central strap 116 having the fastener 114 is wrapped around the wrist region of the user. The lengths of the central strap 116 and the fastener 114 are preferably sufficient to encompass the wrist region at least once. It will be appreciated that, in accordance with one embodiment, the method includes adjusting compression on the wrist region by increasing or decreasing the tightness of the central strap 116 around the wrist region of the user. The method of adjustment facilitates in stabilizing the wrist region of the user.

Figure 4:
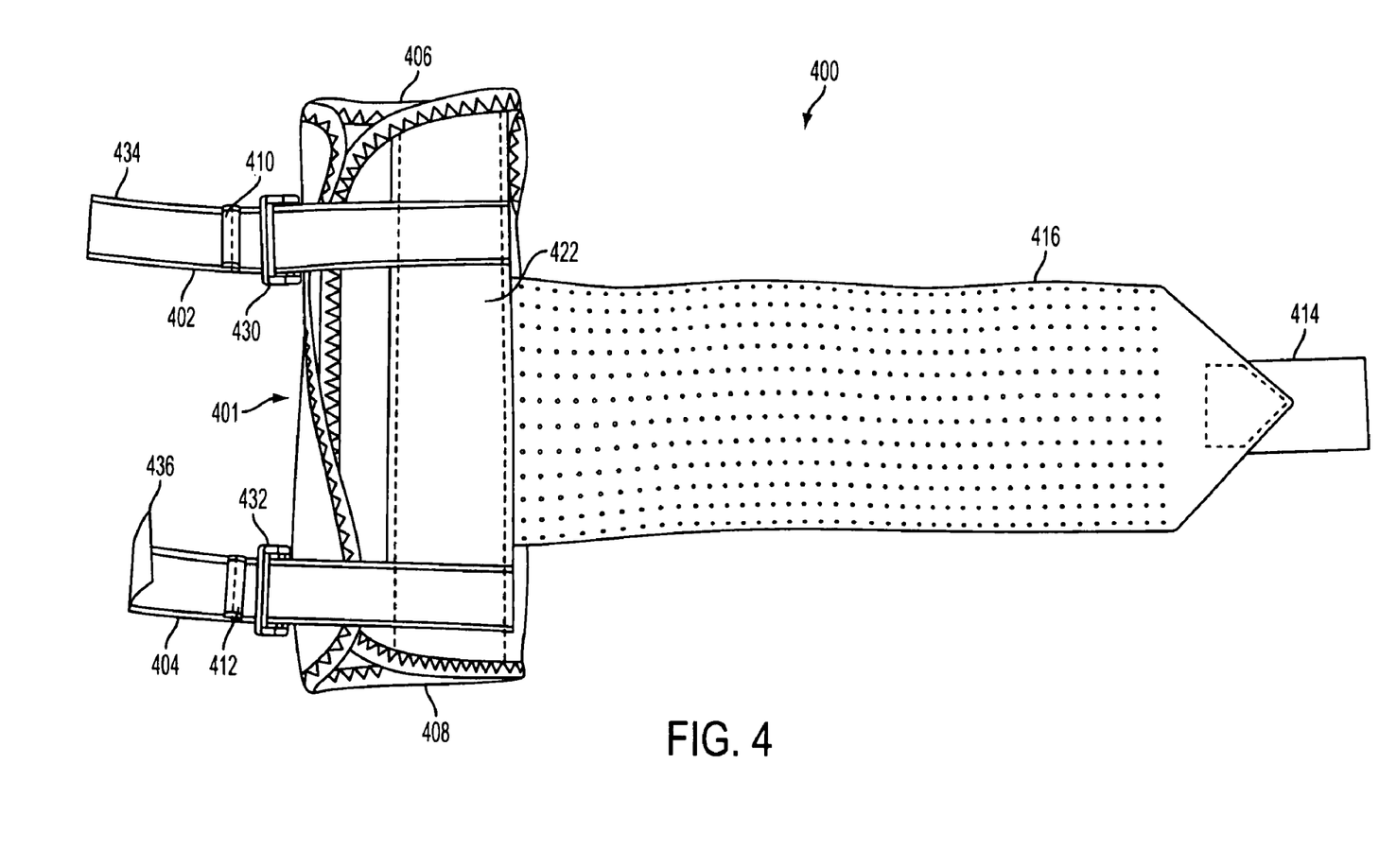
FIG. 4 is a front view of the wrist stabilizer in accordance with an alternate embodiment of the present invention.

FIG. 4 is a front view of the wrist stabilizer 400 in accordance with an alternate embodiment. The wrist stabilizer 400 includes a sleeve 401 which comprises an open upper-end 406, an open lower-end 408, and a thumb opening 424 (shown in FIG. 5). In addition, wrist stabilizer 400 comprises an upper fastener assembly having a strap 402, a lower fastener assembly having a strap 404, and a central strap 416 having a fastener 414. While only three straps are shown in FIG. 4, it will be understood to one of ordinary skill in the art that any number of straps may be used without departing from the spirit and scope of the present invention. The wrist stabilizer 400 is constructed using any natural or synthetic breathable material, including both inelastic and elastic material, having sufficient flexibility and resiliency. The wrist stabilizer 400 may be formed of, for example, Koolflex™ material which provides durability, elasticity, and air-flow. The Koolflex™ material allows the wrist stabilizer 400 to be easily slipped onto a user's hand and more particularly the palm and wrist regions. According to an exemplary embodiment, the Koolflex™ material has a thickness of approximately ⅛ inch. The wrist stabilizer 400 as disclosed in FIG. 4 is similar to the wrist stabilizer 100 as disclosed earlier with respect to FIG. 1; however, the wrist stabilizer 400 is of a different shape and size providing extended protection for the forearm region.

Figure 5:
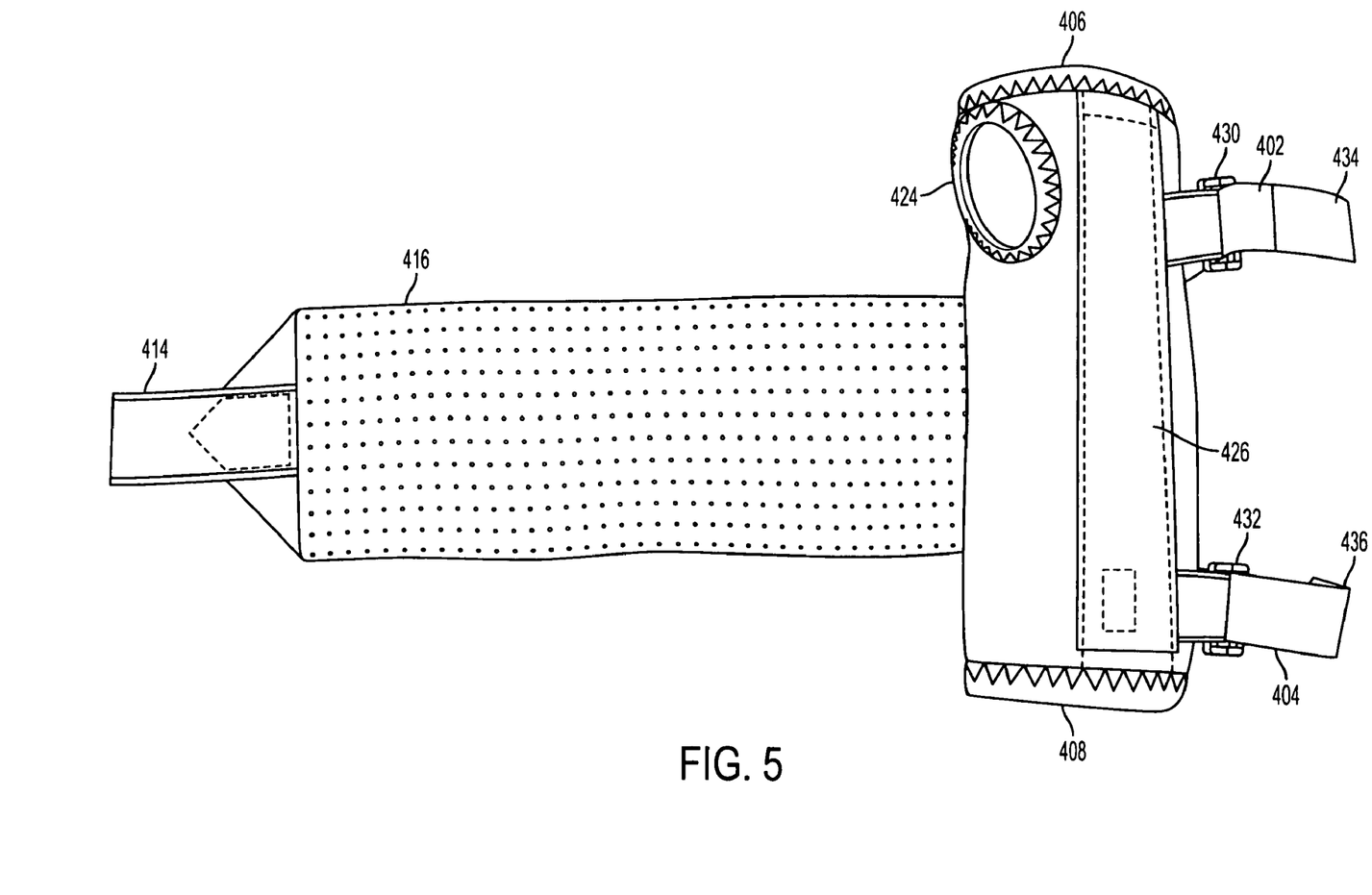
FIG. 5 is a back view of the wrist stabilizer in accordance with an alternate embodiment of the present invention.

FIG. 5 is a back view of the wrist stabilizer 400 of FIG. 4 in accordance with an alternate embodiment of the present invention. Details of the wrist stabilizer 400 have been disclosed with respect to FIG. 4 above.

Figure 6:
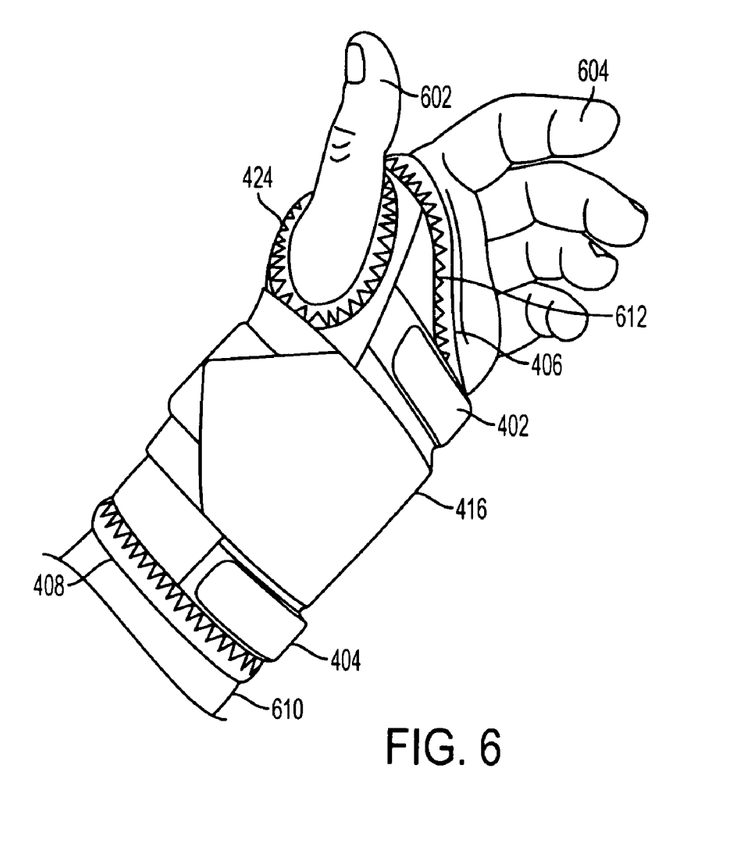
FIG. 6 is a perspective view of the wrist stabilizer placed on a user's hand in accordance with an alternate embodiment of the present invention.

FIG. 6 is a perspective view of the wrist stabilizer 400 placed on a user's hand in accordance with an embodiment of the present invention. The wrist stabilizer 400 is adapted to be slipped onto the user's hand such that the fingers 604 pass through the open upper-end 406 while the thumb 602 passes through the thumb opening 424. According to an exemplary embodiment, the edge 612 of the wrist stabilizer 400 has a curved configuration to accommodate a users palm region. Such curved configuration provides added comfort and extra degree of finger movement when the wrist stabilizer 400 is placed on the user's hand. The upper strap 402 is adapted to secure a palm region of the users hand while the lower strap 404 is adapted to secure a forearm region 610 of the users hand. The central strap 416 having the fastener 414 is wrapped around the wrist region of the user. The lengths of the central strap 416 and the fastener 414 are preferably sufficient to encompass the wrist region at least once. It will be appreciated that compression may be adjusted to a desired level by increasing or decreasing the tightness of the central strap 416 around the wrist region of the user.

The method of operation of the wrist stabilizer 400 in conjunction with FIG. 6 will now be discussed. The wrist stabilizer 400 is adapted to be slipped onto the user's hand such that the fingers 604 pass through the open upper-end 406 while the thumb 602 passes through the thumb opening 424. Once the wrist stabilizer 400 is properly placed over the user's hand, the straps 402 and 404 are wrapped around palm and forearm regions of the user while the central strap 416 is wrapped around a wrist region of the user. The length of the straps 402, 404, and 416 are preferably sufficient to encompass the palm, forearm, and wrist regions at least once. It will be appreciated that compression may be adjusted to a desired level by increasing or decreasing the tightness of the straps 402, 404, and 416 around the palm, forearm, and wrist regions.

Figure 7:
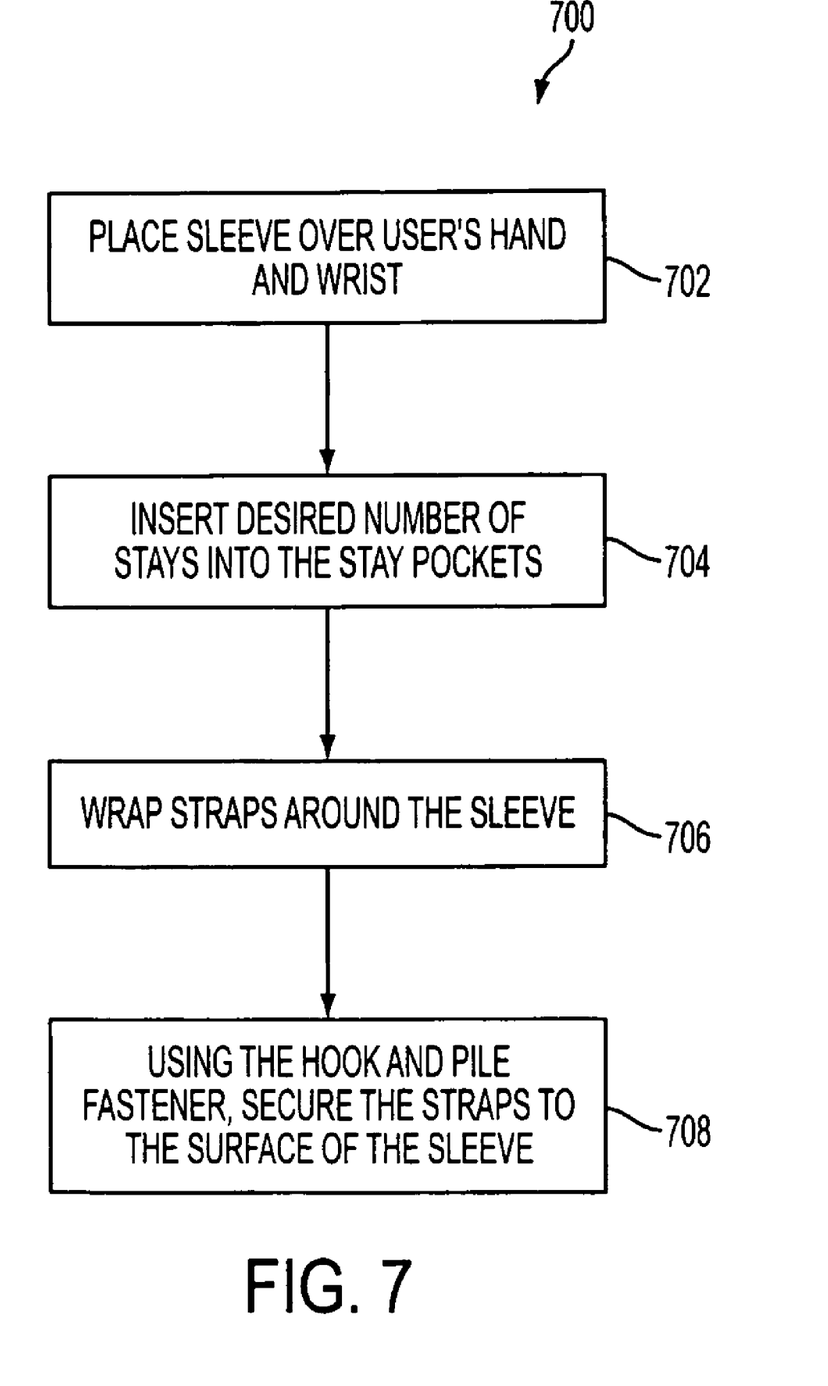
FIG. 7 is a flow diagram illustrating a method of using a wrist stabilizer in accordance with an embodiment of the present invention.

Referring now to FIG. 7, there is shown a flow diagram illustrating a method 700 of using wrist stabilizer 100 and wrist stabilizer 400. First, in step 702, the sleeve 101 or 401 is placed over the wrist and hand of the wearer. Next, in step 704, the desired number of stays are inserted into the desired stay pockets. In step 706, the straps are wrapped around the sleeve 101 or 401 to the desired level of compression. Finally, in step 708, the straps are secured to the surface of the sleeve using the hook and pile fasteners.

It should be noted that the term "hook and pile fasteners" is a recognized structure to one skilled in the art and is often sold under the trademark Velcro®. It is well known that the hook and pile material engage one another. It addition, various surface designs, patterns, and colors may be used as well as various thickness of the Koolflex™ material. Likewise, the present invention is not limited to the use of the Koolflex™ material as other materials may prove satisfactory in their use as wrist stabilizers. The size and shape of the wrist stabilizer 100, 400 as shown herein are exemplary embodiments and other cutout shapes and clearance designs may be utilized in order to accommodate various hand sizes.

Although various embodiments of the method and apparatus of the present invention have been illustrated in the accompanying Drawings and described in the foregoing Detailed Description, it will be understood that the invention is not limited to the embodiments disclosed, but is capable of numerous rearrangements, modifications, and substitutions without departing from the spirit of the invention as set forth herein.

What is claimed:

1. An orthopedic support device of a type worn generally on a hand of a wearer, allowing at least one of a thumb and fingers of the wearer to be substantially unrestricted, the device comprising:
   a unitary sleeve, the unitary sleeve comprising a tubular envelope being of a continuous tubular construction such that the unitary sleeve remains tubular in shape both when worn and when not worn, the unitary sleeve comprising an open upper end for slidably receiving the fingers, an adjacent thumb opening for slidably receiving the thumb, and an open lower end for slidably receiving a wrist of the wearer, the unitary sleeve having first and second loops attached thereto;
   a first strap, disposed near the open upper end of the unitary sleeve and passing through the first loop, the first strap having a first fastener disposed at its distal end and a first enlarged region operable to prevent the first strap from becoming disengaged from the first loop, the first strap operable to be removably wrapped and secured about a portion of the unitary sleeve covering a palm of the wearer, wherein the portion of the unitary sleeve covering the palm of the wearer comprises a curved configuration for added comfort and allows extra degree of finger movement for the wearer;
   a second strap, disposed near the open lower end of the unitary sleeve and passing through the second loop, the second strap having a second fastener disposed at its distal end and a second enlarged region operable to prevent the second strap from becoming disengaged from the second loop, the second strap operable to be removably wrapped and secured about a portion of the unitary sleeve covering a portion of a forearm of the wearer;
   a third strap, disposed between the first strap and the second strap, the third strap having a third fastener disposed at its distal end, the third strap operable to be removably wrapped and secured about a portion of the unitary sleeve covering the wrist of the wearer, the third strap having a width that is more than double that of the first and second straps and wherein the third strap comprises a length substantially longer than that of the first and second straps to encompass the wrist of the wearer at least once;
   a first stay pocket disposed on a surface of the unitary sleeve covering the palm of the wearer;
   a second stay pocket disposed on a dorsal surface of the unitary sleeve; and
   wherein first, second and third straps have anchored ends along an edge of the first stay pocket.

2. The device of claim 1, wherein the unitary sleeve comprises a breathable mesh material.

3. The device of claim 2, wherein the unitary sleeve comprises nylon neoprene.

4. The device of claim 1, further comprising:
   a plurality of stays, each stay of the plurality of stays is capable of being selectively inserted into at least one of the first stay pocket or the second stay pocket.

5. The device of claim 1, wherein the first fastener, the second fastener, and the third fastener each comprise a hook portion and a pile portion.

6. An orthopedic support device of a type worn generally on at least one of a wrist, a palm, and a forearm of a wearer, allowing a wearer's thumb and fingers to be substantially unrestricted, the device comprising:
   a unitary sleeve, the unitary sleeve comprising a tubular envelope being of a continuous tubular construction such that the unitary sleeve remains tubular in shape both when worn and when not worn;
   the unitary sleeve comprising an open upper end for slidably receiving the wearer's fingers, an adjacent thumb opening for slidably receiving the wearer's thumb, and an open lower end for slidably receiving the forearm of the wearer, the unitary sleeve having a first loop and a second loop attached thereto;
   wherein a portion of the unitary sleeve covering the palm of the wearer comprises a curved configuration for added comfort and allows extra degree for finger movement for the wearer;
   a first strap, disposed near the open upper end of the unitary sleeve and passing through the first loop, the first strap having a first fastener disposed at its distal end and a first enlarged region operable to prevent the first strap from becoming disengaged from the first loop, the first strap operable to be removably wrapped and secured about a portion of the unitary sleeve covering the palm of the wearer;

a second strap, disposed near the open lower end of the unitary sleeve and passing through the second loop, the second strap having a second fastener disposed at its distal end and a second enlarged region operable to prevent the second strap from becoming disengaged from the second loop, the second strap operable to be removably wrapped and secured about a portion of the unitary sleeve covering the forearm of the wearer;

a third strap, disposed between the first strap and the second strap, the third strap having a third fastener disposed at its distal end, the third strap operable to be removably wrapped and secured about a portion of the unitary sleeve covering the wrist of the wearer, the third strap having a width that is more than double that of the first and second straps and wherein the third strap comprises a length substantially longer than that of the first and second straps to encompass the wrist of the wearer at least once;

a first stay pocket disposed on a surface of the unitary sleeve covering the palm of the wearer;

a second stay pocket disposed on a dorsal surface of the unitary sleeve; and wherein first, second and third straps have anchored ends along an edge of the first stay pocket.

7. The device of claim 6, wherein the unitary sleeve comprises a breathable mesh material.

8. The device of claim 7, wherein the unitary sleeve comprises nylon neoprene.

9. The device of claim 6, further comprising:

a plurality of stays, each stay of the plurality of stays is capable of being selectively inserted into at least one of the first stay pocket or the second stay pocket.

10. The device of claim 6, wherein the first fastener, the second fastener, and the third fastener each comprise a hook portion and a pile portion.

11. A method for providing orthopedic stabilization to a wrist of a wearer, the method comprising:

providing an orthopedic stabilization device comprising a unitary sleeve, a plurality of straps, and first and second loops, wherein the unitary sleeve comprises a tubular envelope being of a continuous tubular construction such that the unitary sleeve remains tubular in shape both when worn and when not worn;

slipping the orthopedic stabilization device over the wearer's hand and wrist;

selectively inserting at least one stay into at least one stay pocket disposed on a dorsal surface of the orthopedic stabilization device;

wrapping a first strap, disposed at an upper end of the unitary sleeve, by passing the first strap through the first loop, about a portion of the unitary sleeve covering a palm of the wearer to a desired compression level;

wrapping a second strap, disposed at a lower end of the unitary sleeve, by passing the second strap through the second loop, about a portion of the unitary sleeve covering a forearm of the wearer to a desired compression level;

wrapping a third strap, disposed between the first strap and the second strap, about a portion of the unitary sleeve covering the wrist of the wearer to a desired compression level, the third strap having a width that is more than double that of the first and second straps and wherein the third strap comprises a length substantially longer than that of the first and second straps to encompass the wrist of the wearer at least once;

removably securing at least one of the first strap, the second strap, and the third strap to the unitary sleeve using a fastener;

wherein the first and second straps include first and second enlarged regions that keep the first and second straps engaged with the first and second loops and prevent the first and second straps from becoming undone during placement on the wearer's wrist; and wherein the first strap, the second strap, and the third strap have anchored ends along an edge of the at least one stay pocket.

12. The method of claim 11, wherein the step of removably securing at least one of the first strap, the second strap, and the third strap comprises engaging a hook portion and a pile portion of the fastener.

13. The method of claim 11, wherein the step of selectively inserting at least one stay further comprises:

removably inserting a first stay into a first stay pocket; and removably inserting a second stay into a second stay pocket, the second stay pocket disposed opposite the first stay pocket.

14. The method of claim 11, wherein the unitary sleeve comprises a breathable mesh material.

* * * * *